United States Patent
Lalgudi et al.

(10) Patent No.: US 9,000,203 B2
(45) Date of Patent: Apr. 7, 2015

(54) SURFACE MODIFYING COMPOSITIONS

(75) Inventors: Ramanathan S. Lalgudi, Westerville, OH (US); Robert J. Cain, Lewis Center, OH (US)

(73) Assignee: Battelle Memorial Institute, Columbus, OH (US)

( * ) Notice: Subject to any disclaimer, the term of this patent is extended or adjusted under 35 U.S.C. 154(b) by 449 days.

(21) Appl. No.: 13/393,303

(22) PCT Filed: Aug. 31, 2010

(86) PCT No.: PCT/US2010/047295
§ 371 (c)(1),
(2), (4) Date: May 14, 2012

(87) PCT Pub. No.: WO2011/026093
PCT Pub. Date: Mar. 3, 2011

(65) Prior Publication Data
US 2012/0271063 A1    Oct. 25, 2012

Related U.S. Application Data

(60) Provisional application No. 61/238,250, filed on Aug. 31, 2009.

(51) Int. Cl.

| | |
|---|---|
| *C07F 7/10* | (2006.01) |
| *C09D 5/00* | (2006.01) |
| *A01N 55/00* | (2006.01) |
| *C09D 5/14* | (2006.01) |
| *C09D 5/16* | (2006.01) |
| *D06M 13/513* | (2006.01) |
| *D06M 13/517* | (2006.01) |

(52) U.S. Cl.
CPC *C09D 5/00* (2013.01); *A01N 55/00* (2013.01); *C09D 5/14* (2013.01); *C09D 5/1662* (2013.01); *D06M 13/513* (2013.01); *D06M 13/517* (2013.01); *D06M 2200/11* (2013.01)

(58) Field of Classification Search
CPC ......... C07F 7/10; C07F 7/1892; C07F 7/1836
USPC ....................................................... 556/414
See application file for complete search history.

(56) References Cited

U.S. PATENT DOCUMENTS

| | | |
|---|---|---|
| 3,650,816 A | 3/1972 | Rudy et al. |
| 4,191,674 A | 3/1980 | Wismer et al. |
| 4,918,210 A | 4/1990 | Fenton et al. |
| 5,645,883 A | 7/1997 | Russell et al. |
| 2004/0029834 A1* | 2/2004 | Schiestel et al. ................ 514/63 |
| 2004/0029978 A1 | 2/2004 | Chane-Ching |
| 2008/0286628 A1 | 11/2008 | Briehn et al. |

FOREIGN PATENT DOCUMENTS

| | | |
|---|---|---|
| DE | 19756906 A1 | 7/1999 |
| WO | 200236701 A1 | 5/2002 |
| WO | 2004037944 A1 | 5/2004 |
| WO | WO 2004037944 A1 * | 5/2004 |
| WO | 2007070380 A2 | 6/2007 |
| WO | 2008082735 A1 | 7/2008 |

* cited by examiner

*Primary Examiner* — Porfirio Nazario Gonzalez
*Assistant Examiner* — Kofi Adzamli
(74) *Attorney, Agent, or Firm* — MacMillan, Sobanski & Todd, LLC

(57) ABSTRACT

A surface modifying composition comprises an amphiphilic compound which is non-cellulose based, the amphiphilic compound including a covalently linked ionic moiety with the following formula: where M=metal oxide or binary metal oxide, Ai is selected from compounds with surface energy greater than or equal to 25 dynes cm$^{-1}$, A2 is selected from compounds with surface energy greater than or equal to 12 dynes cm$^{-1}$, A3 is selected from compounds having more than one reactive functional group, x=NH$_2$, NHR' or NR'$_2$ (R'=methyl, ethyl, propyl or isopropyl), y=COOH, SO$_3$H or PO$_3$H, and R=H or halogen; and where one of the A$_1$-x, A$_2$, or A$_3$-y may be replaced by a second O—R.

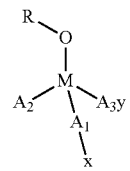

12 Claims, No Drawings

SURFACE MODIFYING COMPOSITIONS

CROSS-REFERENCE TO RELATED APPLICATION

This application claims the benefit of U.S. Provisional Application No. 61/238,250, filed Aug. 31, 2009, the disclosure of which is incorporated herein by reference.

BACKGROUND OF THE INVENTION

The present invention relates to surface modifying compositions that may be applied to surfaces to protect, enhance or otherwise modify the surfaces.

Various types of surface modifying compositions are known. For example, such compositions include UV protectants, corrosion inhibitors, stain repellents, antimicrobial coatings, and others.

In some cases the surface modifying compositions are based on compounds that have low surface energies. However, this low surface energy, which provides a desired modification of the surface, may also present issues of adherence of these compositions to the surfaces on which they are applied.

Also, in some cases the surface modifying compositions have hydrophobic properties that can make it difficult to produce a water based application matrix with the compositions.

Therefore, it would be desirable to provide improved surface modifying compositions.

SUMMARY OF THE INVENTION

A surface modifying composition comprises an amphiphilic compound which is non-cellulose based, the amphiphilic compound including a covalently linked ionic moiety with the following formula:

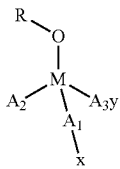

where M=metal oxide or binary metal oxide,
$A_1$ is selected from compounds with surface energy greater than or equal to 25 dynes cm$^{-1}$,
$A_2$ is selected from compounds with surface energy greater than or equal to 12 dynes cm$^{-2}$,
$A_3$ is selected from compounds having more than one reactive functional group,
x=NH$_2$, NHR' or NR'$_2$ (R'=methyl, ethyl, propyl or isopropyl),
y=COOH, SO$_3$H or PO$_3$H, and
R=H or halogen; and
where one of the $A_1$-x, $A_2$, or $A_3$-y may be replaced by a second O—R.

DETAILED DESCRIPTION OF THE PREFERRED EMBODIMENT

A surface modifying composition is provided comprising an amphiphilic compound which is non-cellulose based. As is well known, amphiphilic compounds have a water-soluble polar head (hydrophilic) and a water-insoluble organic tail (hydrophobic). The amphiphilic compound can include any suitable hydrophilic and hydrophobic portions, many of which are well known.

The amphiphilic compound includes a covalently linked ionic moiety with the following structural formula:

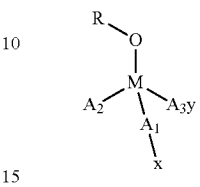

where M=metal oxide or binary metal oxide,
$A_1$ is selected from compounds with surface energy greater than or equal to 25 dynes cm$^{-1}$,
$A_2$ is selected from compounds with surface energy greater than or equal to 12 dynes cm$^{-1}$,
$A_3$ is selected from compounds having more than one reactive functional group, x=NH$_2$, NHR' or NR'$_2$ (R'=methyl, ethyl, propyl or isopropyl),
y=COOH, SO$_3$H or PO$_3$H, and
R=H or halogen; and
where one of the $A_1$-x, $A_2$, or $A_3$-y may be replaced by a second O—R. In certain embodiments the composition includes all of the $A_1$-x, $A_2$, and $A_3$-y groups.

In the structural formula shown above, $A_1$ can be selected from any suitable compound(s) with surface energy greater than or equal to 25 dynes cm$^{-1}$. In certain embodiments, $A_1$ is selected from one or more of alkylene oxides. In some particular embodiments, the alkylene oxides are selected from the group consisting of ethylene oxide, propylene oxide, tetra methylene glycol, aliphatic hydrocarbons such as propyl, isopryl, lauryl, steryl; hydroxyalkyl amines such as tetra(2-hydroxypropyl)ethylenediamine and amino containing silanes such as trimethoxy[3-(methylamino)propyl]-silane, (N,N-dimethylaminopropyl)-trimethoxysilane, (3-aminopropyl)triethoxysilane, N-[3-(trimethoxysilyl)propyl]-ethylenediamine, 3-[Bis(2-hydroxyethyl)amino]propyl-triethoxysilane solution, and amino functional poly (dimethylsiloxane).

In the structural formula, $A_2$ can be selected from any suitable compound(s) with surface energy greater than or equal to 12 dynes cm$^{-1}$. In certain embodiments, $A_2$ is selected from one or more of perfluoroalkyl groups, poly (dimethyl siloxane), poly(tetrafluoro ethylene), and poly(vinyl carbazole).

In the structural formula, $A_3$ can be selected from any suitable compound(s) having more than one reactive functional group. In certain embodiments, the compounds having more than one reactive functional group are selected from the group consisting of hydroxyl containing carboxylic acids, and hydroxyl containing sulfonic acids.

The ionic moiety of the surface modifying composition can have any suitable ionic properties. In certain embodiments, the ionic moiety is anionic, cationic, zwitterionic and/or amphoteric.

Also, the ionic moiety of the surface modifying composition can have any suitable form. In certain embodiments, the ionic moiety is a particulate with particle size ranging between 20 nm and 500 microns. In certain embodiments, the ionic moiety is a particulate with metal and/or non-metal counter ions.

Further, in certain embodiments the ionic moiety comprises a silicon-containing compound.

The surface modifying compositions can have any suitable molecular weights. In certain embodiments, the compositions have molecular weight above $3 \times 10^2$ g mol$^{-1}$ but below $3 \times 10^6$ g mol$^{-1}$.

The surface modifying compositions can have any suitable solubility characteristics. In certain embodiments, the compositions are substantially insoluble in water and organic solvents.

The surface modifying compositions can be prepared by any suitable method, such as any of the methods described in the examples hereinbelow. Different methods of making ionic compounds (namely surfactants and ion exchange resins) are well known and are exemplified in the following patents which are incorporated by reference herein: U.S. Pat. Nos. 5,645,883, 4,918,210 and 4,066,592.

In a particular example, the surface modifying composition is made by hydrophobic modification of compounds containing cationic subunits. In yet another example, the surface modifying composition is made by hydrophobic modification of compounds containing zwitterionic subunits. In another example, cationic compounds with reactive functional groups are modified to obtain surface modifying compositions. For example, the cationic compound with functional group can be reacted with functionally derived poly(dimethylsiloxane) and/or fluoropolymer to obtain amphiphilic cationic compositions.

The surface modifying compositions have been found to provide desired surface modifying properties when applied to substrates. For example, the compositions may protect, enhance or otherwise modify the surfaces. In certain embodiments, the compositions provide excellent oil and water repellent properties. Also, in certain embodiments, the compositions have a compatibility with both aqueous and non-aqueous systems. The surface modifying compositions have excellent adhesion to many substrates. In certain embodiments, the binding affinity of the compositions is ≥0.5 Kcal mole$^{-1}$.

In another embodiment, there is provided a method of applying the surface modifying composition to a substrate. The composition can be applied in any manner suitable for the particular substrate to achieve the desired properties, for example by spraying, immersion or other well known application methods. Depending on the end use, the composition may be applied to the substrate to get the benefits either permanently or temporarily.

The surface modifying composition can have many different uses. Some nonlimiting examples include use as UV protectants, corrosion inhibitors, oil and/or water repellents, stain repellents, antimicrobial coatings, and many others. For example, the surface modifying composition may be applied to materials or substrates such as carpets, glasses, furniture, paper, shoes, fabrics, and vehicle components (e.g. decking, leather, metal/painted metal surfaces). Some particular applications include carpet cleaners, glass cleaners, furniture cleaners, paper, boxes, furniture polish, decking sealant/protectant, leather care products, shoe care products, hair care products, skin lotions, surface treatments for medical products, automotive, boat, or recreational vehicles, anti-icing coating for substrates such as radar domes and air planes, and as well as to resist and repel chemical and biological warfare agents. Some potential market sectors for the stain repellent include automotive, chemical, energy, pharmaceutical, medical and others.

Certain aspects of the surface modifying composition will now be illustrated with reference to the following non-limiting examples.

EXAMPLES

Example 1

In a clean reaction ampoule containing a magnetic stir bar, charged 4.7 grams of 0.1% (wt/wt) acetic acid in toluene. Tridecafluoro-1,1,2,2-tetrahydrooctyl triethoxysilane (Gelest) 2.0 grams were added dropwise over 3 minute under stirring. The solution was allowed to mix for 5 minutes, and then 2.1 grams of (3-aminopropyl) trimethoxysilane (Fluka) was added dropwise over 3 minutes. The solution was allowed to stir at 300-500 rpm under ambient conditions for 3 days to yield a slightly cloudy colorless solution. The solvent was removed using a rotary evaporator to obtain a solid product then ground into particulate form.

Example 2

In a 250 mL 3-neck roundbottom flask fitted with water condenser, magnetic stirrer, and argon inlet, charged 81.290 grams of anhydrous IPA (Aldrichand 0.0812 grams of glacial acetic acid (EMD). To this mixture 16.0320 grams of tridecafluoro-1,1,2,2-tetrahydrooctyl triethoxysilane (Gelest), 16.0175 grams of (3-aminopropyl) trimethoxysilane (Aldrich) and 8.0256 grams of tetraethyl orthosilicate were added and stirred at 28 deg C. for 12 hours under argon blanket. The reaction product was transferred into a beaker and 10 mL of distilled water was added and set in an oven at 80° C. for overnight to obtain gelled solid. The solids were ball-milled overnight with 25 grams of steel ball bearings to obtain the product in particulate form.

Example 3

In a 250 mL 3-neck round bottom flask fitted with water condenser, overhead stirrer, heating mantle, thermocouple, and argon inlet, charged 21.4 grams of the dimethyloctadecyl [3-(trimethoxysilyl)propyl]ammonium chloride (Aldrich), 12.5 grams of tetraethyl orthosilicate (Aldrich), 80.2 grams of anhydrous IPA (Aldrich) and 0.0930 grams of glacial acetic acid. The solution was stirred at 28 deg C. for 12 hours under argon blanket. The reaction product was transferred into a beaker and 10 mL of distilled water was added and set in an oven at 80° C. for overnight to obtain gelled solid. The solids were ball-milled overnight with 25 grams of steel ball bearings to obtain the product in particulate form.

Example 4

In a 250 mL 3-neck round bottom flask fitted with water condenser, overhead stirrer, heating mantle, thermocouple, and argon inlet, charged 35.5 grams of 3-(Triethoxysilyl) propyl isocyanate (Aldrich), 14.6 grams of N,N,-Bis(2-hydroxyethyl)-2-aminoethanesulfonic acid (Aldrich), 50.2 grams of Toluene (BDH). The reactants are heated up to 60° C. under argon purge, with stirring for 12 h followed isolating the product by conventional filtration.

Example 5

In a 250 mL 3-neck roundbottom flask fitted with water condenser, overhead stirrer, heating mantle, thermocouple, and argon inlet, charged 24.4 grams of 3-(Triethoxysilyl)

propyl isocyanate (Aldrich), 10.0 grams of N,N,-Bis(2-hydroxyethyl)-2-aminoethanesulfonic acid (Aldrich), and rinsed in with 56.8 grams of NMP (Aldrich). The reactants are heated up to 170° C. under argon purge, with stirring for 3 h followed isolating the product by conventional filtration.

Example 6

In a 250 mL 3-neck round bottom flask fitted with water condenser, overhead stirrer, heating mantle, thermocouple, and argon inlet, charged 4.0 grams of N,N,-Bis(2-hydroxyethyl)-2-aminoethanesulfonic acid (Aldrich), 60.8 grams of NMP (Aldrich), 7.8 grams of tetraethyl orthosilicate (Aldrich). The reactants were heated to 170° C. under argon purge, and constant stirring. When the solution reached 170° C., 9.7 grams of 3-(Triethoxysilyl)-propyl isocyanate (Aldrich) was mixed with 20.4 grams of toluene, then slowly charged into the flask dropwise over a period of 30 min. After completing the addition of isocyanate, it was allowed to react for 3 hours. After the three hours, the solution was sampled and characterized by infrared spectroscopy for the presence of residual isocyanate peaks and found that the isocyante functional group was not found. To this solution, 10 mL of distilled water was added and allowed to mix at room temp for 12 hours. The product obtained was isolated by conventional methods.

Example 7

In a 250 mL 3-neck roundbottom flask fitted with water condenser, overhead stirrer, heating mantle, thermocouple, and argon inlet, charged 33.1 grams of 3-(Triethoxysilyl) propyl isocyanate (Aldrich), 17.0 grams of (2-Hydroxyethyl)-trimethylammonium chloride (Aldrich), and 50.3 grams of Toluene (BDH). The reactants are heated up to 60° C. under argon purge, with stirring for 12 h followed isolating the product by conventional filtration.

Example 8

Anti-Icing Coating Formulations

In a Flaktek container, 81 grams of 1 part silicone resin (Dow 92007) and 3 grams of Aeroxide LE3 fumed silica were combined and mixed for 1 minute at approximately 2800 rpm using a Flaktek High-Sheer Mixer. One gram of molybdenum disulfide (MoS2) (Climax Molybdenum) was added to the container and the above components were mixed for 1 minute more at approximately 2800 rpm. Ten milliliters of silica particle Solution from Example 1 were added and mixed again at approximately 2800 rpm for 1 minute. The resulting formulation was applied on aluminium coupon and dried at room temperature for 3 days. The coating had contact angle 118 deg with surface roughness 139 microns and ice accumulation reduction factor of 2.7. The control Al coupon had contact angle 70 deg with surface roughness less than 50 microns and ice accumulation reduction factor of 1.

Example 9

Chemical And Stain Repellent Coatings

In a 100 mL 3-neck roundbottom flask fitted with water condenser, magnetic stirrer, and argon inlet, charged 4 grams of Tridecafluoro-1,1,2,2-tetrahydrooctyl triethoxysilane (Gelest) 4 grams of (3-aminopropyl) trimethoxysilane, (Aldrich), and 20 grams of anhydrous isopropanol combined with 0.01 grams of glacial Acetic acid. The solution was mixed rapidly overnight. The clear solution was diluted the next day to 1% wt solids in 100 grams total anhydrous IPA solution, This solution was spray coated onto a 11×11" square piece of test fabric 428 using a DeVillibis HVLP staring line detail gun and dried at room temperature for 12 hours. The treated fabric had a water contact angle of 151 degrees.

Fabric treated with this coating showed very high resistance to the permeability of 1,5-dichloro-3-thiapentane. The effective reduction of 1,5-dichloro-3-thiapentane permeability was 91% less than the untreated control fabric over a 1 hour exposure period. Samples were spiked with 300 µg of 1,5-dichloro-3-thiapentane and immediately capped, then air was passed underneath the fabric swatch and measured with pyrolysis mass spectrometer. Only 24.79 µg passed thru the treated sample, versus 275.8 µg for the control.

Fabric treated with this coating showed very high resistance to oleophobic stains. The treated fabric showed an effective reduction of Sudan IV red dye-olive oil stain solution (difference in color DeltaE=7.78) compared to a control average of DeltaE=55.82, or a stain reduction of 86%. Color difference obtained from before versus after L*a*b* Spectrophotometric color values using the following equation:

$$\text{DeltaE} = \sqrt{(L^*_2 - L^*_1)^2 + (a^*_2 - a^*_1)^2 + (b^*_2 - b^*_1)^2}$$

Example 10

Antimicrobial Coatings

Sample 1: In a 250 mL 3-neck roundbottom flask fitted with water condenser, magnetic stirrer, and argon inlet, charged 10.2580 grams of anhydrous isopropanol (Aldrich) and 0.01 grams of glacial acetic acid (EMD). To this mixture 2.0831 grams of tridecafluoro-1,1,2,2-tetrahydrooctyl triethoxysilane (Gelest), 2.1551 grams of (3-aminopropyl) trimethoxysilane (Aldrich) and 8.0256 grams of tetraethyl orthosilicate were added and stirred at 28 deg C. for 12 hours under argon blanket. The product was coated to a glass slide and cured at 120 deg C. for 1 hour.

Sample 2: In a 100 mL 3-neck round bottom flask fitted with water condenser, overhead stirrer, heating mantle, thermocouple, and argon inlet, charged 2.86 grams of the dimethyloctadecyl[3-(trimethoxysilyepropyl]ammonium chloride (Aldrich), 1.67 grams of tetraethyl orthosilicate (Aldrich), 79.65 grams of anhydrous IPA (Aldrich) and 0.1242 grams of glacial acetic acid. The solution was stirred at 28 deg C. for 12 hours under argon blanket. The product was coated to a glass slide and cured at 120 deg C. for 1 hour.

The coated glass slides obtained from the above example showed very good resistance to *pseudomonas aeruginosa* compared to uncoated glass slides. The uncoated glass slides has 9% dead count where as for sample 1 the dead count was 51% and for sample 2 the dead count was 73%.

The invention claimed is:

1. A surface modifying composition comprising an amphiphilic compound which is non-cellulose based, the amphiphilic compound including a covalently linked ionic moiety with the formula

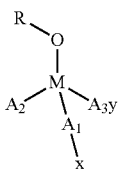

where M=silicon-containing metal oxide or binary metal oxide, $A_1$ is selected from compounds with surface energy greater than or equal to 25 dynes cm$^{-1}$, $A_2$ is selected from compounds with surface energy greater than or equal to 12 dynes cm$^-$, $A_3$ is selected from compounds having more than one reactive functional group, x=NH$_2$, NHR' or NR'$_2$ (R'=methyl, ethyl, propyl or isopropyl), y=COOH, SO$_3$H or PO$_3$H, and R=H or halogen.

2. A composition according to claim 1 wherein $A_1$ is selected from one or more of alkylene oxides.

3. A composition according to claim 2 wherein the alkylene oxides are selected from he group consisting ethylene oxide, propylene oxide, tetramethylene glycol, aliphatic hydrocarbons; hydroxyalkyl amines and amino containing silanes.

4. A composition according to claim 1 wherein $A_2$ is selected from one or more of perfluoroalkyl groups, poly(dimethyl siloxane), poly(tetrafluoro ethylene), and poly(vinyl carbazole).

5. A composition according to claim 1 wherein $A_3$ is selected from the group consisting of hydroxyl containing carboxylic acids, and hydroxyl containing sulfonic acids.

6. A composition according to claim 1 wherein the ionic moiety is anionic, cationic, zwitterionic and/or amphoteric.

7. A composition according to claim 6 wherein the ionic moiety is an anionic, cationic, zwitterionic and/or amphoteric particulate with particle size ranging between 20 nm and 500 microns.

8. A composition according to claim 6 wherein the ionic moiety is an anionic, cationic, zwitterionic and/or amphoteric particulate with metal and/or non-metal counter ions.

9. A composition according to claim 1 having a binding affinity ≥0.5 Kcal mole$^{-1}$.

10. A composition according to claim 1 which is substantially insoluble in water and organic solvents.

11. A method of modifying the surface of a substrate comprising applying to the substrate a surface modifying composition according to claim 1.

12. A composition according to claim 1 wherein R=halogen.

* * * * *